United States Patent [19]
Glorioso et al.

[11] Patent Number: 5,849,571
[45] Date of Patent: Dec. 15, 1998

[54] LATENCY ACTIVE HERPES VIRUS PROMOTERS AND THEIR USE

[75] Inventors: Joseph C. Glorioso, Cheswick; David J. Fink; William F. Goins, both of Pittsburgh, all of Pa.

[73] Assignees: University of Pittsburgh of the Commonwealth System of Higher Education, Pittsburgh, Pa.; Regents of the University of Michigan, Ann Arbor, Mich.

[21] Appl. No.: 401,638

[22] Filed: Mar. 8, 1995

Related U.S. Application Data

[63] Continuation-in-part of Ser. No. 995,842, Dec. 23, 1992, abandoned, which is a continuation of Ser. No. 856,868, Mar. 24, 1992, abandoned, which is a continuation of Ser. No. 595,041, Oct. 10, 1990, abandoned.

[51] Int. Cl.$^6$ .................................................. C12N 15/00
[52] U.S. Cl. .................................. 435/320.1; 435/172.3; 935/57
[58] Field of Search ........................... 514/44; 435/240.2, 435/320.1, 235.1, 172.3; 424/93.1; 536/24.1; 935/62, 57

[56] References Cited

U.S. PATENT DOCUMENTS

| | | |
|---|---|---|
| 4,970,155 | 11/1990 | Okasinski . |
| 5,672,344 | 9/1997 | Kelley et al. . |
| 5,674,722 | 10/1997 | Mulligan et al. . |

FOREIGN PATENT DOCUMENTS

| | | |
|---|---|---|
| 176170 | 4/1986 | European Pat. Off. . |
| 243155 | 10/1987 | European Pat. Off. . |
| 282330 | 9/1988 | European Pat. Off. . |
| 300422 | 1/1989 | European Pat. Off. . |
| 453242 | 10/1991 | European Pat. Off. . |
| 477056 | 3/1992 | European Pat. Off. . |
| WO 90/02551 | 3/1990 | WIPO . |
| WO 90/06757 | 6/1990 | WIPO . |
| WO 90/09441 | 8/1990 | WIPO . |
| WO 91/02788 | 3/1991 | WIPO . |

OTHER PUBLICATIONS

E. Marshall (1995) Science 269:1050–1055.
Vile et al (1995) Targeted Gene Therapy 9:190–199.
Chen et al., "Alternative Promoters for the Latency–Associated Transcripts of HSV–1" (Abstract 388), 19$^{th}$ International Herpesvirus Workshop, Vancouver, B.C. (Jul.–Aug., 1991).
French et al., "Identification of Cis–and Trans–Acting Elements in the TATA–less Latency Active Promoter of Herpes Simplex Type–1" (Abstract 386), 19$^{th}$ International Herpesvirus Workshop, Vancouver, B.C. (Jul.–Aug., 1991).
Glorioso et al, "Developments of Herpes Simplex Virus Vectors for Gene Transfer to the General Nervous System" pp. 281–302, in *Gene Therapeutics: Methods and Application of Direct Gene Transfer,* (J.A. Wolff,, ed.) (Birkhäuser, 1995).
Glorioso et al, "Herpes Simplex Virus Vectors and Gene Transfer to Brain" pp. 79–87, in *Recombinant Vectors in Vaccine Development,* vol. 82 (F. Brown, ed.) (Dev. Biol. Stand., 1994).
Glorioso et al., "Developments of Herpes Simplex Virus as a Gene Transfer Vector for the Central Nervous System," pp. 133–145, in *Gene Transfer and Therapy in the Nervous System* (Gage & Christian, eds.) (Springer–Verlag, 1992).
Glorioso et al., *Seminars in Virol.,* 3, 265–76 (1992).
Goins et al., "Characterization and Expression of the Herpes Simplex Virus Latency Specific Promoter in Neuronal Tissue" (Abstract), 14$^{th}$ International Herpesvirus Workshop, Nyborg Strand, Denmark, (1989).
Goins et al., "Characterization of a Novel TATAless Latency Active Promoter of Herpes Simplex Virus Type–1" (Abstract 8B–02), 18$^{th}$ International Herpesvirus Workshop, Pittsburgh Pennsylvania (Jul., 1993).
Goins et al., Abstract B405, *J. Biol. Chem., Suppl.,* 15A, 199 (1991).
Goins et al., *J. Virol.,* 68(4), 2239–52 (1994).
Ramakirshnan et al., *J. Virol.,* 68(3), 1864–73 (1994).
Sternberg et al., "HSV–Mediated Gene Transfer into Rat CNS" (Abstract 8B–02), 16$^{th}$ International Herpesvirus Workshop, Pacific Grove, California (Jul., 1991).
Lokensgard et al., *J. Virol.,* 68(11), 7148–58 (1994).
Glorioso et al., *Annals of Neurology,* 35 S28–S34 (1994).
Margolis et al., *Virology,* 197, 585–92 (1993).
Efstathiou, S. et al., *J. Gen. Virol.,* 70, 869–879 (1989).
Efstathiou, S. et al., *J. Virol.,* 57, 446–455 (1986).
Fink, D.J. et al., *Ann. Neurol.,* 28, 220 (1990).
Fink, D.J. et al., *Soc. Neurosci. Abstr.,* 16, 964 (1990).
Frame, M.C. et al., *J. Gen. Virol.,* 68, 2699–2704 (1987).
Freese, A. et al. *Biochem. Pharmacol.,* 40, 2189–2199 (1990).
Friedmann, T., *Science,* 244, 1275–1280 (1989).
Frink et al., *J. Virol.,* 45, 634–647 (1983).
Geller, A. et al., *Science,* 241, 1667–1669 (1988).
Gorman, C.M. et al., *Mol. Cell. Biol.* 2, 1044–1051 (1982).
Hill, J.M. et al., *Virology,* 174, 117–125 (1990).
Hill, T.J., "*The Herpesviruses*" pp. 174–240, Plenum Press, New York (1985).

(List continued on next page.)

*Primary Examiner*—Deborah Crouch
*Attorney, Agent, or Firm*—Leydig, Voit & Mayer, Ltd.

[57] ABSTRACT

The application discloses the structure of a herpes virus promoter that by means of which one can obtain the transcription of a non-herpes gene in a cell latently infected with a herpes virus. An HSV-1 vector comprising a LAP2 promoter encoded by SEQ ID NO:1, or fragments of SEQ ID NO:1 which have LAP 2 promoter activity regulating the expression of a heterologous gene is particularly disclosed. The herpes virus is preferably used to obtain such expression in the neurons of the peripheral nerves, and the ganglion cells of the cranial nerves. The invention teaches that specific diseases and pathological conditions and the corresponding non-herpes genes wherein such expression has practical value.

12 Claims, 6 Drawing Sheets

OTHER PUBLICATIONS

Ho, D.Y. et al., *Proc. Natl. Acad. Sci. USA,* 86, 7596–7600 (1989).
Homa, F.L. et al., *Mol. Cell. Biol.,* 6, 3652–3666 (1986).
Homa, F.L. et al., *Genes and Development,* 2, 40–53 (1988).
Honess, R.W. et al., *Proc. Natl. Acad. Sci. USA,* 72, 1276–1280 (1975).
Honess, R.W. et al., *J. Virol.,* 14, 8–19 (1974).
Jalanko, A. et al., *Gene,* 78, 287–296 (1989).
Leib, D.A. et al., *J. Virol.,* 63, 2893–2900 (1989).
Mann, R. et al., *Cell,* 33, 153–159 (1983).
McFarland, D.J. et al., *J. Nuerol. Sci.,* 72, 307–318 (1986).
McGeoch, et al., *J. Mol. Biol.,* 181, 1–13 (1985).
Mellerick, D.M. et al., *Virology,* 158, 265–275 (1987).
Melton, D.W. et al., *Cell,* 44, 319–328 (1986).
Osborne, W.R.A. et al., *Proc. Natl. Acad. Sci. USA,* 85, 6851–6855 (1988).
Palella, T.D. et al., *Mol. Cell. Biol.,* 8, 457–460 (1988).
Palella, T.D. et al., *Pediatr. Res.,* 24, 129 (1988).
Palella, T.D. et al., *Gene,* 80 137–1444 (1989).
Patel, P.I. et al., *Mol. Cell. Biol.,* 6, 393–403 (1986).
Perry, L.J. et al., *J. Gen. Virol.,* 67, 2365–2380 (1986).
Post and Roizman, *Cell,* 25, 227–232 (1981).
Puga, A. et al., *J. Virol.,* 61, 1700–1703 (1987).
Rixon, F.J. et al., *J. Gen. Virol.,* 71, 2931–2939.
Rock, D.L. et al., *J. Virol.,* 61, 3820–3826 (1987).
Ace, C.I. et al., *J. Virol.,* 63: 2260–2269 (1989).
Anderson, J.R. et al., *J. Neurol. Sci.* 60, 181–195 (1983).
Bak, I.J. et al., *Brain Res.,* 136, 415–429 (1977).
Bender, M.A. et al., *J. Virol.,* 61, 1639–1646 (1987).
Boothman, D.A. et al., *FEBS Lett.,* 258, 159–162 (1989).
Chakrabarti, et al., *Mol. Cell. Bio.,* 5, 3403–3409 (1985).
Chiocca, E.A. et al., *The New Biologist,* 2, 739–746 (1990).
Clements, J.B. et al., *Cell,* 12, 275–285 (1977).
Cone, R.D. et al., *Science,* 236, 954–957 (1987).
Croen, K.D. et al., *N. Engl. J. Med.,* 317, 1427–1432 (1987).
Deatly, A.M. et al., *Proc. Natl. Acad. Sci. USA,* 84, 3204–3208 (1987).
Dealty, A.M. et al. *J. Virol.* 62 749–756 (1988).
Dixon, R.A.F. et al., *J. Virol.,* 36, 189–203 (1980).
Dobson, A. et al., *Nueron,* 5, 353–360 (1990).
Dobson, A. et al., *J. Virol.,* 63, 3844–3851 (1989).
Rock, D.L. et al., *Nature,* 302, 523–525 (1983).
Sabel, B.A. et al., *Soc. Neurosci. Abstr.,* 15, 9 (1989).
Sanes, J.R. et al., *EMBO J.,* 5, 3133–3142 (1986).
Sauer, B. et al., *Proc. Natl. Acad. Sci. USA,* 84, 9108–9112 (1987).
Sederati, F. et al., *J. Virol.,* 63, 4455–4458 (1989).
Shapira, M. et al., *Nuc. Acids Res.,* 15, 3097–3111 (1987).
Shih, M. et al., *Proc. Natl. Acad. Sci. USA,* 81, 5867–5870 (1984).
Smiley, J.R. et al., *J. Virol.,* 61, 2368–2377 (1987).
Spivack, J.G. et al., *J. Virol.,* 61., 3841–3847 (1987).
Steiner, I. et al., *EMBO J.,* 8, 505–511 (1989).
Stevens, J.G. et al., *Science,* 235, 1056–1059 (1987).
Van Zijl, M. et al., *J. Gen. Virol.,* 71, 1747–1755 (1990).
Wagner, E.K. et al., *J. Virol.,* 62, 1194–1202 (1988).
Wagner et al., *Proc. Natl. Acad. Sci.,* 78, 1441–1445 (1981).
Weber, P.C. et al., *Cell,* 54, 369–381 (1988).
Weber, P.C. et al., *Science,* 236, 576–579 (1987).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 697 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
CCTGCAGCCG  GGGCGGCCAA  GGGCGTCGGC  GACATCCTCC  CCCTAAGCGC  CGGCCGGCCG    60
CTGGTCTGTT  TTTTCGTTTT  CCCCGTTTCG  GGGGTGGTGG  GGGTTGCGGT  TTCTGTTTCT   120
TTAACCCGTC  TGGGGTGTTT  TTCGTTCCGT  CGCCGGAATG  TTTCGTTCGT  CTGTCCCCTC   180
ACGGGGCGAA  GGCCGCGTAC  GGCCCGGGAC  GAGGGGCCCC  GACCGCGGCG  GTCCGGGCCC   240
CGTCCGGACC  CGCTCGCCGG  CACGCGACGC  GAAAAAGGCC  CCCCGGAGGC  TTTTCGGGT    300
TCCCGGCCCG  GGGCCTGAGA  TGAACACTCG  GGGTTACCGC  CAACGGCCGG  CCCCGTGGC    360
GGCCCGGCCC  GGGGCCCCGG  CGGACCCAAG  GGGCCCCGGC  CCGGGGCCCC  ACAACGGCCC   420
GGCGCATGCG  CTGTGGTTTT  TTTTTCCTCG  GTGTTCTGCC  GGGCTCCATC  GCCTTTCCTG   480
TTCTCGCTTC  TCCCCCCCCC  CTTCTTCACC  CCCAGTACCC  TCCTCCCTCC  CTTCCTCCCC   540
CGTTATCCCA  CTCGTCGAGG  GCGCCCCGGT  GTCGTTCAAC  AAAGACGCCG  CGTTTCCAGG   600
TAGGTTAGAC  ACCTGCTTCT  CCCCAATAGA  GGGGGGGGAC  CCAAACGACA  GGGGCGCCC    660
CAGAGGCTAA  GGTCGGCCAC  GCCACTCGCG  GGTGGGC                              697
```

LATENCY ACTIVE HERPES VIRUS PROMOTERS AND THEIR USE

This application is a continuation-in-part of application Ser. No. 07/995,842, filed Dec. 23, 1992, now abandoned and which is a continuation of Ser. No. 07/856,868, filed Mar. 24, 1992, now abandoned, which was a continuation of Ser. No. 07/595,041, filed Oct. 10, 1990, now abandoned, which is hereby incorporated by reference in its entirety.

The invention was made with United States Government support and the United States Government has certain rights to the invention.

1. FIELD OF THE INVENTION

The present invention relates to the use of a modified Herpes Simplex Virus to express a gene of interest into a cell of a subject. The invention concerns a replication defective herpes viral vector to express a gene of interest so as to provide therapy for diseases of the nervous system. More particularly, the invention concerns a novel promoter that can be used to express the gene of interest in the dorsal root ganglion cells of the sensory nervous system and in the anterior horn cells of the motor nervous system, when these cells are latently infected by the viral vector. Diseases of the nervous system that can be treated by this means include familial amyotrophic lateral sclerosis, X-linked spinal muscular atrophy, metabolic polyneuropathies such as those associated with diabetes mellitus and toxic polyneuropathies such as those associated with cancer chemotherapy.

2. BACKGROUND OF THE INVENTION

Herpes simplex virus type 1 (HSV-1) is a human neurotropic, enveloped virus possessing 152 kb of linear dsDNA encoding over 70 gene products (Roizman, B., 1990, Virology, 2nd Ed., Raven Press, New York). Primary HSV infection of the skin or mucosal membranes results in virus entry into the peripheral nervous system (PNS) by infectious particle penetration of axon terminals of sensory neurons (Stevens, J. G., 1989, *Microbiol.* Rev. 53:318–332). The virus capsids are transported in a retrograde manner to neuronal cell bodies within the sensory ganglion where the viral genomes are released into the nuclei. The genome can either express lytic functions or remain largely quiescent thereby establishing a state of latency. Under these latter circumstances, the viral genome persists for long periods unless interrupted by induction of the lytic cycle with the subsequent appearance of clinically apparent lesions or asymptomatic shedding of virus at or near the primary site of infection.

It has been an attractive possibility to use a latent or persistent Herpes Virus to express over an extended period of time a gene of interest in a neuronal cell of a subject having a neurological disease. A persistent and heretofore unsolved problem with this approach has been that a gene which has been introduced would be transiently expressed, but thereafter expression ceased on about the 5th through seventh day after infection.

During latency, the viral genome persists as a circular episome (Mellerick, D. M., 1987, *Virology* 158:265–275), condensed into a chromatin-like structure (Deshmane, S. L., 1989, *J. Virol.* 63:943–947) and shows a highly restricted and characteristic pattern of viral gene expression (Hill, T. J., 1985, The herpesviruses, Vol. 3). The only transcriptionally active region recognized maps within the inverted repeat sequences flanking the unique long ($U_L$) termini and thus, this latency gene is diploid. A diverse group of RNAs collectively referred to as the latency associated transcripts or LATs are encoded by this gene (Croen, K. D., 1987, *N. Eng. J. Med.* 317:1427–1432; Gordon, Y. J., 1988, *J. Virol.* 62:1832–1835; Krause, P. R., 1990, *J. Clin. Invest.* 86:235–241; Perry, L. J., 1986, *J. Gen. Virol.* 67:2365–2380; Rock, D. L., 1987, *J. Virol.* 61:3820–3826; Spivack, J. G., 1987, *J. Virol.* 61:3841–3847; Spivack, J. G., 1988, *J. Virol.* 62:1479–1485; Stevens, J. G., 1987, *Science* 235:1056–1059; Wagner, E. K., 1988, *J. Virol.* 62:4577–4585). The LATs overlap the ICP0 immediate early regulatory gene and are transcribed off the opposite DNA stand. Studies of the LATs present in latently infected neurons indicate that they are largely intranuclear, nonpolyadenylated and some of the RNAs are uncapped (Devi-Rao, G. B., 1991, *J. Virol.* 65:2179–2190; Spivack, J. G., 1987, *J. Virol.* 61:3841–3847; Wagner, E. K., 1988, *J. Virol.* 62:4577–4585). The most abundant or major species is approximately 2 kb in length although less abundant 1.5 and 1.45 kb species are also detectible and are presumed to be derived from the 2 kb RNA by splicing (Deatly, A. M., 1988, *J. Virol.* 62:749–756; Mitchell, W. J., 1990, *J. Gen. Virol.* 71:125–132; Spivack, J. G., 1987, *J. Virol.* 61:3841–3847; Wagner, E. K., 1988, *J. Virol.* 62:1194–1202; Wagner, E. K., 1988, *J. Virol.* 62:4577–4585; Wechsler, S. L., 1988, *J.Virol.* 62:4051–4058). The 2 kb LAT has also been observed during lytic infection but the minor species have only been observed during latency.

The LAT region also codes for an 8.77 kb polyA$^+$ transcript found in lytic infection which seems to exist in low abundance in latently infected neurons (Devi-Rao, G. B., 1991, *J. Virol.* 65:2179–2190; Dobson, A. T., 1989, *J. Virol.* 63:3844–3851; Zwaagstra, J. C., 1990, *J. Virol.* 64:5019–5028). It has been suggested that this RNA represents the primary LAT transcript which is subsequently processed to produce the more stable 2.0, 1.5 and 1.45 kb polyA$^-$ species. The 6–7 kb spliced polyA$^+$ product of this reaction has not been observed, however. The sequence surrounding the 5' end of these smaller RNAs is similar to that of the mammalian consensus splice donor site. Introduction of this splicing signal into a reporter gene cassette resulted in proper splicing and transient gene expression in transfection assays (Farrell, M. J., 1991, *Proc. Natl. Acad. Sci. USA* 88:790–794) although it is unknown whether this splice site is used in actual latency. Because the 8.77 kb LAT is difficult to detect in latency, it has been suggested that the readily detected 2 kb LAT is a stable intron processed from the larger, highly unstable polyA$^+$ mRNA. It remains difficult, though, to explain the presence and processing of the additional smaller LATS, which are detected solely during latency since they appear to have identical 5' and 3' termini. Alternatively, these species may arise by usage of different splice donor and acceptor sites. Several studies have been performed to identify and characterize the promoter responsible for LAT expression. The region immediately upstream of the major 2 kb LAT sequence is devoid of the TATA consensus element generally found about 30 bp upstream of the transcription start site for many eukaryotic genes. The nearest TATA box homology is present almost 700 bp upstream of the 5' end of the major 2 kb LAT. Various reports have documented LAT promoter regulatory elements located upstream and within the region of this TATA box (Batchelor, A. H., 1990, *J. Virol.* 64:3269–3279; Batchelor, A. H., 1992, *J. Virol.* 66:3573–3582; Devi-Rao, G. B., 1991, *J. Virol.* 65:2179–2190; Leib, D. A., 1991, *Proc. Natl. Acad. Sci. USA* 88:48–52; Zwaagstra, J. C., 1989, *T. Gen. Virol.* 70:2163–2169.; Zwaagstra, J. C., 1991, *Virology* 182:287–297; Zwaagstra, J. C., 1990, *J. Virol.*

64:5019–5028). These include several Spl sites, a CCAAT box homology (Batchelor, A. H., 1992, J. Virol. 66:3573–3582), and cAMP response (CRE) element (Leib, D. A., 1991, Proc. Natl. Acad. Sci. USA 88:48–52), a sequence homologous to the adenovirus MLTF element USF (Zwaagstra, J. C., 1991, Virology 182:287–297), and a neuronal "enhancer" region (Batchelor, A. H., 1992, J. Virol. 66:3573–3582). Furthermore, recombinant virus in which the β-globin cDNA was inserted 11 bp downstream of the TATA box produced β-globin specific mRNA in latently infected sensory neurons of the PNS (Dobson, A. T., 1989, J. Virol. 63:3844–3851) and deletion of this TATA box containing promoter region eliminated LAT expression in latently infected ganglia (Devi-Rao, G. B., 1991, J. Virol. 65:2179–2190; Dobson, A. T., 1989, J. Virol. 63:3844–3851). Additionally, sequence comparison between HSV-1 and HSV-2 showed that the TATA box promoter region and the 3' end of the 2 kb displayed the highest degree of homology (Krause, P. R., 1991, J. Virol. 65:5619–5623) between the two strains, although the high level of 3' end homology could be due to the fact that this sequence is also present within the coding sequence of ICP0. These experiments, together, support the conclusion that the LAT promoter lies within the region containing the TATA box and are consistent with evidence that the major 2 kb LAT results from splicing of this larger transcript. For purposes of discussion, this far upstream promoter will be referred to as the latency associated promoter 1 or LAP1.

In vivo experiments using a virus in which the β-galactosidase (lacZ) reporter gene was inserted into the LAT region at position +137 relative to the 5' end of the major 2 kb LAT, showed that this recombinant fails to produce β-galactosidase during productive infection, yet displays a punctate staining pattern within latently infected neurons following X-gal staining of mouse trigeminal ganglia tissue sections (Ho, D. Y., 1989, Proc. Natl. Acad. Sci. USA 86:7596–7600). RNase mapping studies demonstrated that the chimeric mRNA initiated near the 5' end of the stable LATS, rather than the expected start site downstream of the LAP1 TATA box. Thus, lacZ expression may be induced by a previously undescribed promoter located more proximal to the 5' end of the 2 kb LAT. Moreover, recent characterization of the 5' and 3' ends of the stable LATs (Spivack, J. G., 1991, J. Virol. 65:6800–6810) showed that the 5' end maps to a G residue 1 nucleotide removed from the proposed splice donor sequence (CAG/GTAG) in agreement with the initial RNA mapping work (Wagner, E. K., 1988, J. Virol. 62:1194–1202), but in contrast to that seen in other studies (Krause, P. R., 1990, J. Clin. Invest. 86:235–241; Krause, P. R., 1991, J. Virol. 65:5619–5623). In addition, the 3' end maps approximately 79 bp upstream from the proposed splice acceptor site (Farrell, M. J., 1991, Proc. Natl. Acad. Sci. USA 88:790–794), a region devoid of a consensus splice acceptor and branch point signals. This is in contrast to previous mapping studies (Devi-Rao, G. B., 1991, J. Virol. 65:2179–2190) which place the 3' end of the 2 kb LAT at or near the proposed splice acceptor site. These recent results suggest that the 2.0, 1.5 and 1.45 kb LATs may represent bona fide transcripts rather than introns merely being processed from the larger 8.77 kb transcript. If this were the case, a second promoter would need to be present within sequences between LAP1 and the 2 kb LAT 5' terminus.

3. SUMMARY OF THE INVENTION

The present invention provides a recombinant herpes virus that is replication defective except on complementary cell lines because one or more of the immediate early genes of the virus are inoperable and preferably deleted. The recombinant virus contains a gene of interest encoding a non-herpes protein, which gene is operably linked to a herpes latency active promoter that is found between the LAP1 promoter and the 2 kb LAT 5' terminus (hereinafter the "LAP2" promoter).

The invention further provides methods whereby the recombinant virus is introduced into the cell body of a motor or sensory neuron of a peripheral nerve so that the virus is latent and the latency active promoter causes the expression of the gene of interest. In appropriate subjects, the gene of interest can be selected to have a therapeutic effect.

4. DESCRIPTION OF THE FIGURES

FIG. 1(A–E). Summary of 5' deletion analysis of LAP2. FIG. 1A depicts the location of the LAT region is shown within the internal repeat region bracketing the long unique ($U_L$) segment of HSV-1. The restriction map of the region containing relevant restriction sites is depicted including numbering of the sites according to the nucleotide position from the left-hand end of the prototype genome. Note that the PpuMI site has been changed to a BamHI site in our LAT region clone. FIG. 1B depicts the transcription pattern of the LAT region. The RNA transcripts of the HSV-1 genes ICP0, ICP34.5 and the 3' half of ICP4 are depicted. The LAT sequences are transcibed from the opposite strand of ICP0, ICP34.5 and ICP4. The 8.77 kb polyadenylated transcript is present during productive infection. The stable 2 kb LAT transcript, also detected during acute infection, is the major transcript during latency. The smaller 1.5 kb RNA represents a spliced variant found exclusively during latent infection. The splice donor (SD) and acceptor (SA) sites are shown along with the position limits of the LAT RNAs. FIG. 1D and 1E are CAT plasmids lacking LAP2 sequence.

FIG. 4 depicts the location of ICP4::Tn5#15 and ICP4::Tn5#23 within the wt ICP4 molecule. The coding sequence (open box) within the ICP4 message contains two regions of extensive homology with varicella zester virus immediate early gene 62 depicted in black, as well as a nuclear localization signal and the regions of the molecule involved in transactivation.

FIG. 5. Construction of gC⁻::LAP2-lacZ and d120 (ICP4⁻), gC⁻::LAP2-lacZ. A diagram of the viral recombinants containing the LAP2-lacZ cassette in the ectopic gC locus of wt KOS and the ICP4 mutant d120 (DeLuca, N. A. et al., 1985, *J. Virol.* 56:558–570) are depicted at the top of the figure. LAP2 (PstI to BamHI; −597 to +42) was cloned upstream of the β-galactosidase (lacZ) reporter gene producing the plasmid pLAP2-lacZ. A PstI-BamHI fragment containing the LAP2-lacZ chimera was cloned into a plasmid, pGC-1, that contains the promoter and coding sequence for the glycoprotein C (gC) late gene in a manner that removed all of the gC promoter. This construct, pgC:LAP2-lacZ, was recombined into the genome of wt KOS or d120 (ICP4⁻) (DeLuca, N. A. et al., 1985, *J. Virol.* 56:558–570) by standard marker transfer (Homa, F. L. et al., 1986, *Mol. Cell. Biol.* 6:3652–3666) to produce the recombinants gC⁻::LAP2-lacZ and d120 (ICP4⁻),gC⁻::LAP2-lacZ respectively. The location of relevant restriction sites and the various HSV gene products within the XhoI A fragment are shown.

5. DETAILED DESCRIPTION OF THE INVENTION

The invention provides a replication defective or attenuated herpes simplex virus, type-1, having a gene of interest recombinantly inserted into the virus, wherein the gene of interest is operably linked to a promoter that causes the gene to be expressed in a neuron of a mammalian host for an extended period of time, e.g., for more than 80 days and preferably for more than 250 to 300 days. Only the gene of interest is expressed; there is substantially no production of viral proteins in the host neuron. For this reason the virus is termed latent.

The invention provides a latency active promoter, which is comprised of a sequence hereinafter termed LAP2 that is found in the region of about 600 bp immediately 5' of the 5' terminus of the LAT. In addition to LAP2 sequences the latency active promoter can have other sequences such as LAP1 sequences or sequences of other enhancers. The presence of LAP1 sequences is not essential. In the present invention it is to be understood that in certain embodiments of the invention the latency active promoter contains a deletion of portions of the LAP2 sequence, e.g., in the region from about 195 bp 5' of the LAT 5' terminus and about 400 bp 5' of the LAT 5' terminus. Even though a portion of the LAP2 is deleted from such a latency active promoter, it nonetheless is to be regarded as having a LAP2 sequence.

In an embodiment of the invention the latency active promoter and the gene of interest are inserted into the herpes virus genome between two exons of a single structural gene of the virus or between the promoter and its corresponding structural gene. In the invention, the insertion disrupts a structural gene that is expressed during the replication of the virus. In a preferred embodiment the insertion disrupts a structural gene that is essential for viral replication.

The invention further provides a recombinant nucleic acid construct having a latency active promoter operably linked to a gene of interest, which gene includes a 3' untranslated region. The promoter and gene are flanked by portions of a herpes gene or genes that is or are expressed during the replication of the virus. The construct is termed hereinafter a "cassette". In a preferred embodiment of the invention the gene of interest is present in a cassette wherein the replication expressed viral gene is a viral gene that is essential for viral replication.

Within the scope of the invention are nucleic acids having cassettes that are present as an insert in a bacterial cloning vector, which are useful so that the cassette can be amplified, and cassettes which are be present in a herpes virus genome.

A cassette can be inserted into a herpes virus genome by homologous recombination between the viral genome and cassette. The homologous recombination can be performed by co-transfection of the cassette and a herpes virus genome into a cell line that supports the replication of the virus encoded by the viral genome and selection of recombinant viruses. Recombinant viruses can be identified by plaque hybridization according to the method of Ho, D. Y., 1989, *Proc. Natl. Acad. Sci.* 86:7596. Alternatively the cassettes can be inserted at a predetermined site by use of the cre-lox recombinase system.

The herpes virus can be made replication defective by a muatation or deletion of a gene that is essential for replication of the virus. Particular examples include deletion of some or all of the immediate early gene genes of the virus, e.g., ICP0, ICP4 or ICP27. Stocks of replication defective vectors can be grown on complementing cell lines, which are cell lines that have had a copy of the essential viral gene incorporated into their genome. Attenuated viruses are viruses that replicate in non-neuronal tisseus, e.g., the corneal epithelium, but are not able to sustain a productive infection in neuronal cells, particularly not within cells of the central nervous system. Herpes virus that lack a functional thymidine kinase gene, a Us3 gene or a ribonucleotide reductase gene are examples of attenuated viruses.

5.1. ROUTES OF INTRODUCTION OF VIRUS

It is an object of the present invention to express a therapeutic gene of interest in the cell body of a neuron of a peripheral nerve. The cell bodies of peripheral nerve neurons are located in the dorsal root ganglia, for sensory neurons, and in the anterior columns of the spinal cord, the anterior horn motor neuron cells. Replication defective virus particles can be introduced into a large proportion of the neurons that innervate a particular area by intramuscular or intradermal injection within the particular area. For example, the ganglion cells of the trigeminal ganglion can be infected by injection of virus into the stroma of the eye. Alternatively, the virus can be introduced by direct injection into a peripheral nerve itself.

5.2. THERAPEUTIC GENES AND CORRESPONDING PATHOLOGICAL CONDITIONS

The diseases and pathological conditions that can be treated by the present invention are of two types. The first type are genetic diseases wherein a mutant gene is expressed in the anterior horn cell and thereby causes the pathological process. Examples of such diseases include X-linked spinal muscular atrophy (Fischbeck, K. H., et al., 1991, *Adv. Neurol.* 56:209–13) which is caused by a mutation in the androgen receptor and familial amyotrophic lateral sclerosis (Borchelt, D. R. et al., 1994, *Proc. Natl. Acad. Sci.* 91:8292) which is caused by a mutation in the ZnCu-superoxide dismutase gene (SOD1). The invention provides therapies for these and similar conditions, which may be hereafter discovered, by providing a means of specifically introducing and expressing a copy of the normal gene in the affected neuronal cell having the mutated gene.

The second type of pathological condition, for which the invention provides a treatment, are pathological conditions in which an abnormal or pharmacologic amount or level of expression of a protein is therapeutic. Examples are polyneuropathies, such as are found in diabetes mellitus and are also found, frequently, as a complication of cancer therapy with vinblastine, vincristine or cis-platinum. These neuropathies are considered to be, in principle, responsive to therapy by increased levels of neurotrophic factors. Similarly, muscular diseases caused by degenerative changes in the anterior horn cells have been considered appropriate for treatment by neurotrophic factors.

However, considerable practical difficulties have been noted because of the adverse effects caused by the systemic administration of the neurotrophic factors. These adverse effects can be, in large part, overcome if the production of the neurotrophic factor is confined to the affected neuronal cell bodies as is made possible by the invention.

The neurotrophic factors suitable for use in the invention and where their sequences have been published include β-NGF (GENBANK V01511, Ullrich, A., et al., 1983, Nature 303:821–25), ciliary neurotrophic factor (GENBANK X55889, Lam, A., et al., Gene 102:271–76), brain derived neurotrophic factor (GENBANK M61176, Maisonpierre, P. C., 1991, Genomics 10:558–68), neurotrophin-3 (GENBANK M61189, Id), and glial cell dervied neurotrophic factor (GENBANK L19063 L15306, Lin,L.-F. H., et al., 1993, Science 260:1130).

The same range of diseases can also be treated by expressing a gene encoding the receptors for neurotrophic factors. The genes encoding the receptors for nerve growth factor (trkC), for brain derived neurotrophic factor (trkB) have been identified. Reviewed in Ip, Y. T., & Yancopoulas, G. D., 1994 Curr. Opin. Neurobiol. 4:400; Saltiel, A. R., & Decker, S. J., 1994, Bioessays 16:405–11. The cloning of the receptor for ciliary neurotrophic growth factor has recently been published. Panayotatos, N., et al., 1994, Biochemistry 33:5813.

In yet a further embodiment of the invention a subject having an intractable pain of neurogenic origin, e.g., trigeminal neuralgia or a herpes infection of a dorsal root ganglion (shingles), can be treated by expression of a gene encoding preproenkephalin in the effected sensory ganglion cells.

6. EXAMPLES

6.1. MATERIALS AND METHODS

Plasmid Construction. This report combines transient gene expression data which were derived in two independent laboratories and thus, two independent sets of wild-type and deletion mutant promoter constructs are described. One set of LAP2-CAT gene plasmids was engineered at the University of Michigan and the other was constructed at the National Institute of Allergy and Infectious Disease (NIAID).

The Michigan LAT promoter-CAT reporter constructs shown in FIG.1, Part D, were produced by cloning the PstI (genomic nucleotide position #118867) to KpnI (#119963) restriction fragment from strain KOS into pUC19 at those respective sites in the pUC19 polylinker. The PpuMI site at +42 relative to the 5' end of the 2 kb LAT (#119500) was converted into a BamHI site using Klenow polymerase (BRL, Gaithersburg, Md.) and phosphorylated BamHI linkers (NEB, Beverly, Mass.) (Sambrook, J., 1989, Cold Spring Harbor Press); and, a battery of restriction endonucleases in combination with BamHI were used to subclone the putative LAP2 region into a plasmid containing a loxp recombination site, pBS65-lox (Gage, P. J., 1992, J. Virol. 66:5509–5515; Sauer, B., 1987, Proc. Natl. Acad. Sci. USA 84:9108–9112). The pSVOCAT (Gorman, C. M., 1982, Mol. Cell Biol. 2:1044–1051) plasmid was modified to include a BglII site 5' of CAT, and the 1.6 kb BglII-BamHI fragment containing the CAT gene linked to the SV40 polya signal was cloned downstream of the engineered BamHI site (+42) in each promoter test plasmid. Internal deletion mutations were produced by partial digestion of the −597/+42 promoter-CAT construct with the restriction enzyme SmaI (BRL) followed by religation according to the conditions described by the supplier (BRL). The −800/+42 construct was produced by cloning the 203 bp PstI fragment at the upstream PstI site in the −597/+42 (PstI-BamHI)-CAT construct. A promoterless control plasmid was constructed to contain the 1.6 kb CAT gene cloned into the BamHI site of a pBS65-lox plasmid.

Figures 1A, 1B:
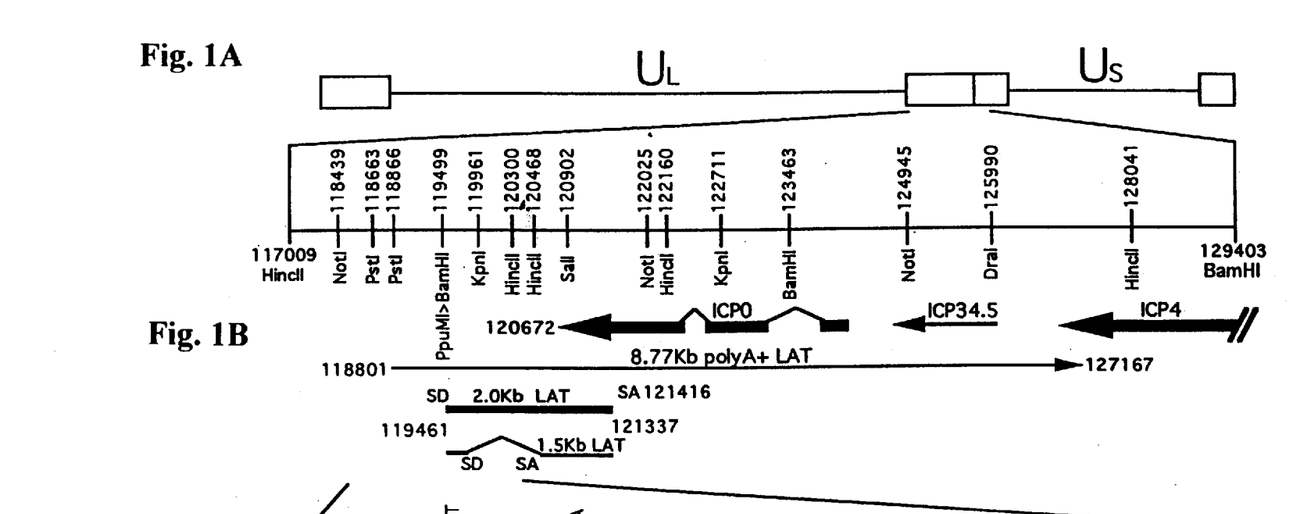
Figure 1C:
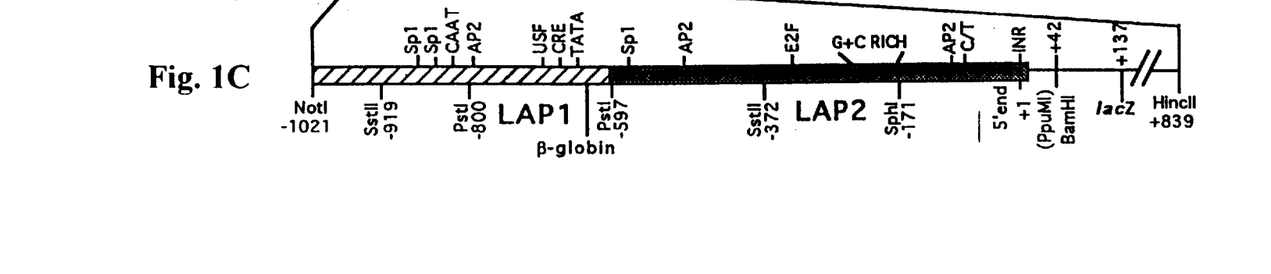
FIG. 1C depicts of LAP1 (SstII-SstII) and LAP2 (PstI-BamHI) regulatory regions and known cis-elements. Relevant restriction sites are shown and numbered referring to the 5' end of the 2 kb LAT RNA as +1. The location of the β-globin insertion downstream of the LAP1 TATA box (Dobson, A. T. et al. 1989, J. Virol. 63:3844–3851) and the insertion of lacZ downstream of LAP2 in the RH142 recombinant (Ho, D. Y. et al., 1989, Proc. Natl. Acad. Sci. USA 86:7596–7600) are shown.
Figure 1D:
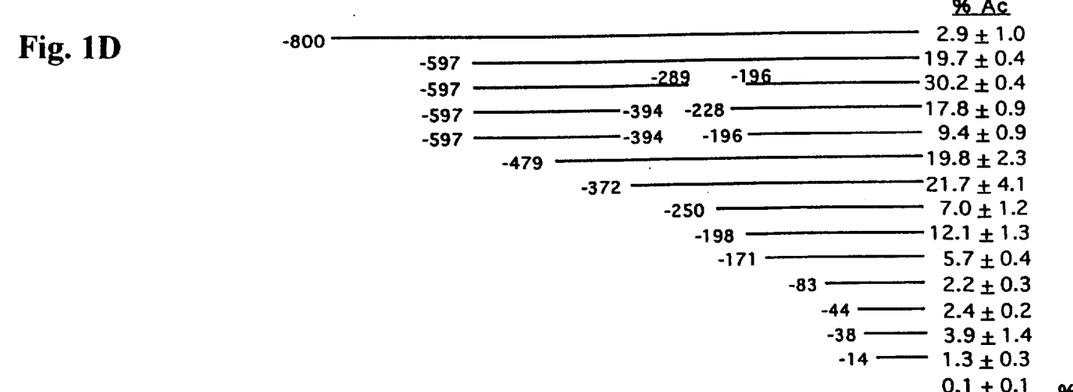
FIG. 1D dspicts the CAT activity of 5' end and internal deletion nutants of LAP2. The 5' end limits of each construct are shown and the 3' limit of these constructs was the BamHl site at +42. Activity is represented as percent acetylation (%Ac).
Figure 1E:
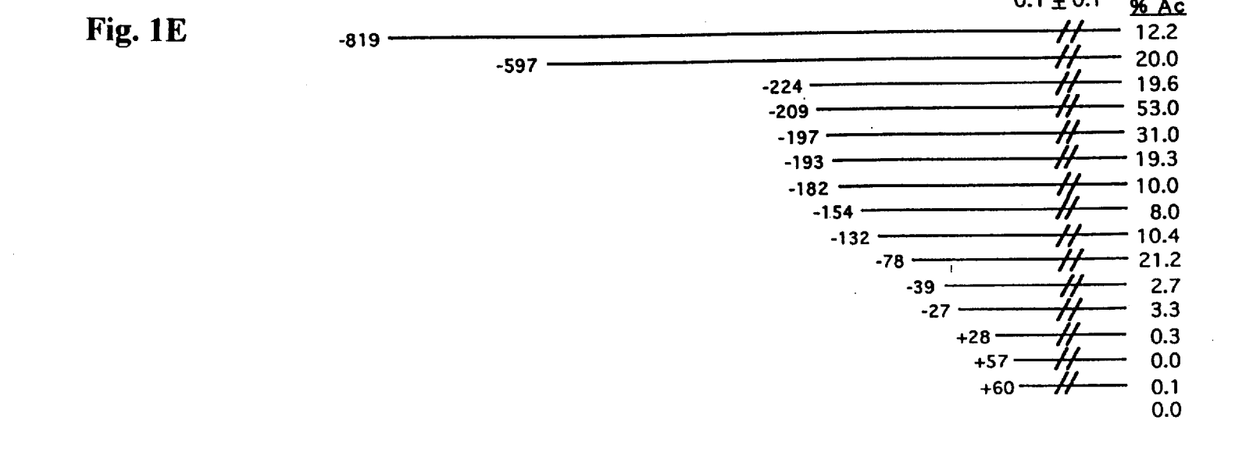
FIG. 1E depicts the CAT activity of 5' end deletion mutants using the HincII site (+839) as the 3' limit of each construct. The final CAT constructs in both parts

The NIH LAT promoter-CAT reporter gene constructs detailed in FIG. 1E, were engineered by cloning restriction fragments representing the LAT region into a background plasmid pCAT (Rosenthal, N., 1987, Methods Enzymol. 152:704–720) containing the CAT reporter gene cloned into the HindIII site of pGEM-3Z (Promega, Madison, Wis.). The 3' limit of these constructs was the HincII site (#120300) at +839 relative to the 5' end of the 2.0 kb stable LAT transcript. A majority of the constructs were produced by Bal31 (BRL) digestion (Sambrook, J., 1989, Cold Spring Harbor Press) of the AvaI-HincII clone (−197/+839) that was previously cloned with AvaI. The 5' terminus of each construct contained in the library of clones produced by Bal31 digestion was determined by DNA sequence analysis.

The plasmid CAT reporter constructs containing LAP1 TATA box containing promoter sequences were produced by cloning specific LAT region restriction fragments into either the PCAT (Promega) background (Rosenthal, N., 1987, Methods Enzymol. 152:704–720) or by insertion into pBS65-lox (Gage, P. J., 1992, J. Virol. 66:5509–5515; Sauer, B., 1987, Proc. Natl. Acad. Sci. USA 84:9108–9112) followed by insertion of CAT as described above for the LAP2-CAT constructs.

Figure 4:
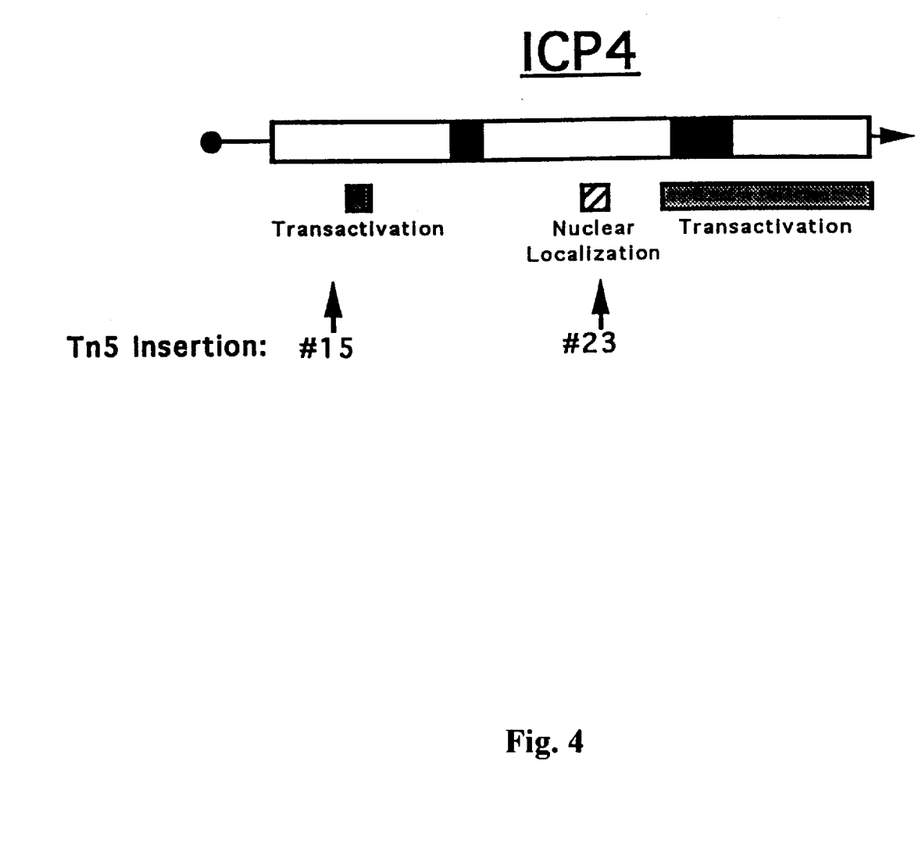
Figure 5:
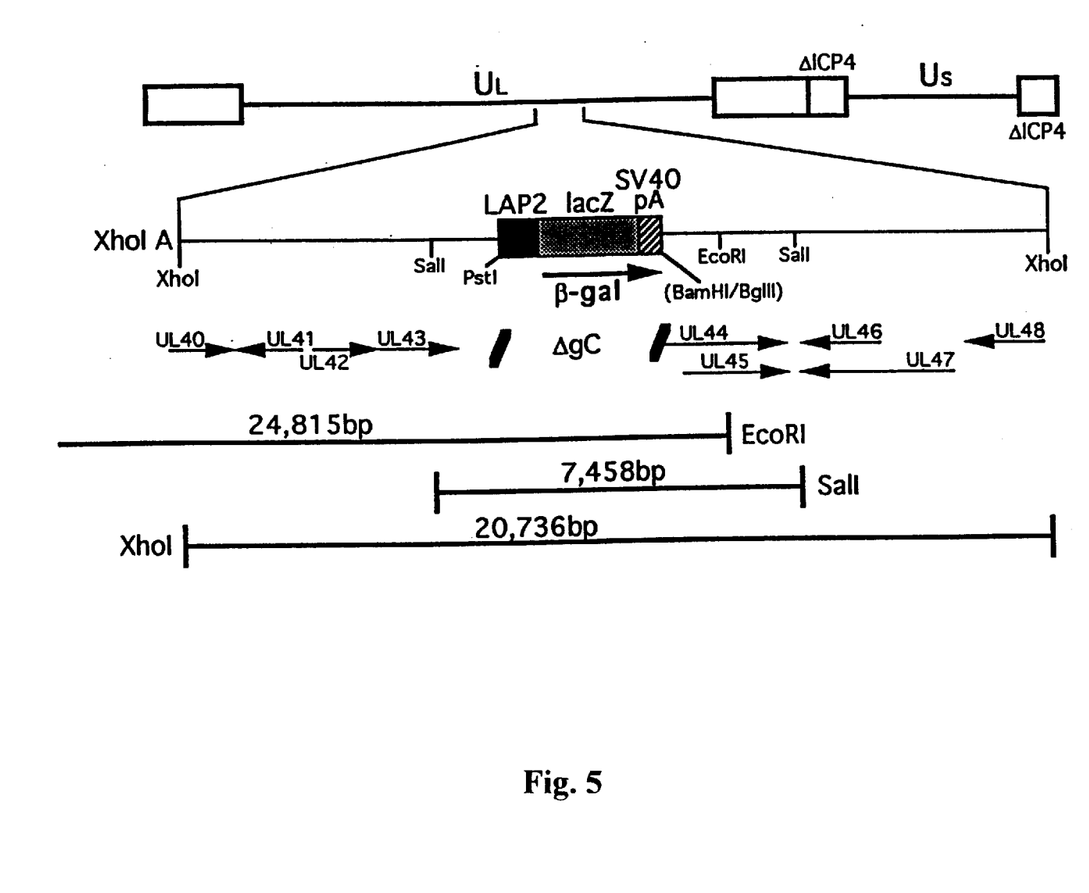

Construction of TnS Insertion Mutants. The plasmid pSG1-EK1 (Quinlan, M. P., 1985, Cell Biol. 5:957–963) containing the ICP4 immediate early regulatory gene was subjected to Tn5 mutagenesis as previously described (Weber, P. C., 1987, Science 236:576–579) using the λ467::Tn5 carrier phage technique of deBruijn and Lupski (deBruijn, F. J., 1984, Gene 27:131–149). The location of the Tn5 inserts within pSG1-EK1 was confirmed by restriction endonuclease digestion. Two specific insertion mutants detailed in FIG. 4 were used in cotransfection experiments along with the test promoter-CAT constructs.

Transfections and CAT Assays. Transfections and CAT assays indicated in FIG. 1D were carried out at the University of Michigan and the University of Pittsburgh, while those indicated in FIG. 1E were performed at the NIH. For the assays involving the Michigan constructs 5 μg of plasmid were transfected into Vero (African green monkey kidney) cells in duplicate using the calcium phosphate precipitation method of Graham and van der Eb (Graham, F. L., 1973, Virology 52:456–467) and a 20% glycerol shock according to the method of Shapira et. al (Shapira, M., 1987, Nucl. Acids Res. 15:3097–3111). Cell lysates harvested at 48 hours post transfection (h.p.t.) were assayed for CAT activity, the percent conversion of radiolabeled substrate chloramphenicol to the acetylated products quantitated and normalized to protein content (BIORAD, Richmond Calif.) (Bradford, M. M. 1976, Anal. Biochem. 72:248–254) as previously described (Shapira, M., 1987, Nucl. Acids Res. 15:3097–3111). Experiments testing individual promoter constructs were repeated at least four times and the results represent the average percent acetylation. Transfections and CAT assays performed using the NIH constructs were identical to those conditions used for the Michigan constructs except 10 $\mu$g of reporter plasmid was used rather than 5 $\mu$g.

Cotransfection and Transfection/Infection Assays. Vero cells were transfected in duplicate as detailed above using 5 $\mu$gs of the promoter-CAT plasmids with equimolar amounts of various effector gene plasmids as previously described (Shapira, M., 1987, Nucl. Acids Res. 15:3097–3111). The plasmids pSG1-EK1 (provided by D. Knipe) (Quinlan, M. P., 1985, Cell Biol. 5:957–963) and PIGA 15 (provided by S. Silverstein) (Gelman, I. H., 1985, Proc. Natl. Acad. Sci. USA 82:5265–5269), containing the sequences which encode the HSV-1 immediate early gene transactivating gene products ICP4 and ICP0 respectively, were used as effector plasmids in cotransfection assays. The control reporter plasmid pgC-CAT, contained the SalI-BglII fragment [−1313 to +124] of the HSV-1 glycoprotein C (gC) late gene promoter from the plasmid pGC (Homa, F. L., 1986, Mol. Cell. Biol. 6:3652–3666; Shapira, M., 1987, Nucl. Acids Res. 15:3097–3111) fused to CAT. For the transfection/infection assays Vero cells were transfected in duplicate with 5 $\mu$gs of promoter-CAT plasmid and the transfected cell monolayers infected with wild-type HSV-1 (KOS) at a multiplicity of five 24 h.p.t. Twenty four hours later (48 h.p.t.), cell lysates were harvested and analyzed for CAT activity as described above.

RNAse Protection Assays. To produce single-stranded probes for the RNAse protection assays, a 475 bp SphI (−171)—EcoRI (+250 of CAT) fragment from the −597/+42 LAP2-CAT construct was cloned into the SphI/EcoRI sites of the plasmid pSP72 (Promega). All in vitro transcribed probes were synthesized with [$\alpha^{32}$P] CTP using the MAXIscript kit (Ambion, Austin, Tex.). Antisense CRNA probes were produced from this clone using T7 RNA polymerase and template linearized at the XhoI site in the vector near the SphI site. Sense riboprobe was produced from template linearized at the EcoRI site using SP6 RNA polymerase. Full-length probes were purified on 6% urea denaturing polyacrylamide gels for use in the RNase protection assay. Total cell RNA was isolated from nine 100 mm petri dishes of Vero cells transfected with the −597/+42 LAP2-CAT construct or mock-transfected cells at 48 h.p.t. using the RNAzolB Kit (Cinna/Biotecx, Houston, Tex.). All RNase protection reactions were performed using the RPA-II kit (Ambion) according to the conditions of the kit. Probes were hybridized to 50 $\mu$g of RNA at 48° C. overnight followed by a 30 min digestion at 37° C. with the RNase A+Tl cocktail provided in the kit. Additionally, 10 $\mu$g of TRNA was used as a negative control. Protected hybrids were separated on 6% urea denaturing polyacrylamide gels. The gels were dried and exposed to X-ray film. A $^{32}$P-labeled HinfI digest of pSV325 was used as a marker for these assays.

Construction of Recombinant Viruses Containing Promoter-Reporter Gene Constructs. The PstI-BamHI fragment (−597/+42 of the major 2.0 kb LAT upstream sequence) was cloned upstream of the E.coli β-galactosidase gene (lacZ) in the plasmid pON1 (Spaete, R. R., 1985, J. Virol. 56:135–143) at the sole BglII site to produce the plasmid pLAP2-lacZ. A 4.3 kb PstI-BamHI fragment from pLAP2-lacz, containing the LAT upstream region fused to the lacZ-SV40 polya gene cassette, was cloned into the PstI (−381) and BglII (+124) sites of the glycoprotein C gene plasmid pGC (Homa, F. L., 1986, Mol. Cell. Biol. 6:3652–3666) replacing the gC promoter to produce the plasmid pgC:LAP2-lacZ. This construct contains over 930 bp of 5' and 2.6 kb of 3' flanking sequence for homologous recombination into the viral genome. The pgC:LAP2-lacZ plasmid (2 $\mu$g) was linearized with SalI, coprecipitated with 2 $\mu$g of wild-type HSVl(KOS) DNA or ICP4 deletion (d120) mutant virus (DeLuca, N. A., 1985, J. Virol. 56:558–570) according to the procedure of Graham and van der Eb (Graham, F. L., 1973, Virology 52:456–467) and transfected into Vero or ICP4 deletion mutant complementary E5 cells as previously described (Homa, F. L., 1986, Mol. Cell. Biol. 6:3652–3666). To enrich for recombinants which should be gC-, monoclonal antibodies (mabs) to gC$^-$ (Holland, T. C., 1983, J. Virol. 45:672–682; Marlin, S. D., 1985, J. Virol. 53:128–136) were used to neutralize progeny of the transfection that expressed gC. The neutralization reaction containing 50 $\mu$g of the original transfection supernatant, a 1:500 dilution of gC specific mAb3 C3, C4 and C8 (Holland, T. C., 1983, J. Virol. 45:672–682; Marlin, S. D., 1985, J. Virol. 53:128–136) plus 10% rabbit complement (Cappel, We3t Chester, Pa.) was incubated at 37° C. for 3 h. viral recombinants were selected on the basis of resistance to neutralization in two successive rounds of mAb treatment and subsequent virus propagation. The virus surviving two rounds of neutralization was then plaque purified (Homa, F. L., 1986, Mol. Cell. Biol. 6:3652–3666; Weber, P. C., 1987, Science 236:576–579) and screened by dot blot hybridization using a $^{32}$P-labelled lacZ specific probe as previously described (Hendricks, R. L., 1991, J. Gen. Virol. 72:1601–1610). Virus supernatants from positive recombinants were pooled and subjected to further rounds of plaque purification until pure stocks were achieved. The presence of the LAP2-$^{lac}$Z reporter gene cassette in the gC locus of the recombinants was confirmed by Southern blot analysis (Southern, P. J., 1982, J. Mol. App. Genet. 1:327–341). Viral DNA was isolated from recombinant and wild-type (KOS and d120) infected cells and virions (Goldin, A. L., 1981, J. Virol. 38:50–58), digested with EcoRI, SA1I and XhoI (BRL), subjected to electrophoresis in 1% agarose (BRL) gels, transferred to Nytran membranes (Schleicher & Schuell, Keene, N.H.) and hybridized with a lacZ specific probe (Hendricks, R. L., 1991, J. Gen. Virol. 72:1601–1610). $^{32}$P-labelled probes for Southern and dot blot hybridizations were generated using the Random Primed DNA Labeling Kit (Boehringer Mannheim, Indianapolis, Ind.) and a gel-purified restriction fragment from lacZ. $^{32}$P-labeled λ-DNA digested with Hind-III served as a size standard. The expected bands of 24.8 kb, 7.5 kb, and 20.7 kb were observed in the EcoRI, SalI, and XhoI lanes, respectively.

Cells and Viruses. Vero (African green monkey kidney) and B103 neuroma cells were grown in Eagle's minimum essential medium supplemented with nonessential amino acids and 10% fetal calf serum (Gibco, Long Island, N.Y.) as previously described (Homa, F. L., 1986, Mol. Cell. Biol. 6:3652–3666) Wild-type HSV-1 KOS strain, as well as recombinants in the KOS background (gC$^-$: :LAP2-lacZ) were propagated on Vero cells (Holland, T. C., 1983, J. Virol. 45:672–682) The ICP4 deletion mutant d120 (DeLuca, N. A., 1985, J. Virol. 56:558–570) and the d120 (ICP4$^-$), gC:

:LAP2-lacZ recombinant were propagated on E5 cells as per DeLuca et al. (DeLuca, N. A., 1985, *J. Virol.* 56:558–570).

Expression of the lacZ reporter gene from viral recombinants in cell culture. Vero, E5 and B103 cells in 60 mm dishes were each infected with d120 and d120 (ICP4$^-$),gC$^-$::LAP2-lacZ at multiplicities of 0.001 and 0.1. At 2 and 5 days post-infection β-galactosidase activity was detected by X-gal staining. Cell monolayers were fixed with 4% paraformaldehyde for 15 min at 25° C., rinsed 3 times with Earle's Balanced salt solution (EBSS) (Gibco), reacted with 0.14% X-gal (BRL) in 100 mm Tris pH8.0, 14.3% DMSO, 14 mM K$_4$Fe(CN)6, and 14 mM K$_3$Fe(CN)6 for 24 h at 37° C. and counterstained with 0.1% neutral red (Sigma, St. Louis, Mo.).

Expression of the lacZ reporter gene from viral recombinants in mouse PNS. Female 8- to 12-wk-old A/J strain mice (Jackson Laboratories, Bar Harbor, Me.) were anesthetized with 2 mg of Ketamine hydrochloride (Parke Davis, Morris Plains, N.J.) and 0.04 mg of acepromazine maleate (AVECO, Fort Dodge, Ind.) in 0.1 ml of RPM1–1640 medium (Gibco) injected intermuscularly in the left hind leg. Topical corneal infection was performed following anesthesia by placement of 3 μl containing 1x10$^5$PFU of either KOS or gC$^-$::LAP2lacZ virus on the surface of the abraded cornea. Direct stromal inoculation was performed using 3 μl containing 1×10$^4$PFU of d120 (ICP4$^-$), gC$^-$::LAP2-lacZ. At various times post-inoculation the animals were sacrificed, the trigeminal ganglia and eyes removed, embedded in O.C.T. (Tissue Tek-Miles, Naperville, Ill.), snap-frozen in dry ice/acetone and 6 μm sections cut at –20° C. Sections were either fixed in acetone for immunocytochemistry (Fink, D. J., 1992, *Human Gene Ther.* 3:11–19; Hendricks, R. L., 1991, *J. Gen. Virol.* 72:1601–1610) with anti-HSV (Cappel) and anti-β-galactosidase antisera (Cappel) or fixed in 0.5% glutaraldehyde for X-gal staining as previously described (Fink, D. J., 1992, *Human Gene Ther.* 3:11–19; Hendricks, R. L., 1991, *J. Gen. Virol.* 72:1601–1610; Ho, D. Y., 1989, *Proc. Natl. Acad. Sci. USA* 86:7596–7600).

RT-PCR Analyses. RT-PCR assays were performed using RNA isolated from the trigeminal ganglia of Sprague Dawley rats infected with d120 (ICP4$^-$), gC: :LAP2-lacZ at 7 and 21 days post-infection. Male Sprague Dawley rats (190300 g) were anesthetized with 5% chloral hydrate (i.p. 0.8 ml/100 g body weight), Both cornea were scraped with a 30 g needle tip and 2 μl containing 1.8×10$^6$PFU of the d120 (ICP4$^-$), gC$^-$::LAP2-lacZ recombinant were applied to each cornea. The rats were sacrificed by decapitation at 7 and 21 days post-infection, the trigeminal ganglia removed and immediately frozen in isopentane at –30° C. Several small slices of the trigeminal ganglia were homogenized in TRI Reagent (TRI Reagent Kit, Molecular Research Center, Cincinnati, Ohio) according to the protocol provided in the kit. This kit allows for the isolation of RNA, DNA and protein from the same sample. Precipated RNA was treated with RNase-free DNaseI (Boehringer Mannheim) prior to use in PCR. RNA (RT) PCR analyses were performed on 500 ng of RNA using primer pairs for glycoprotein B (gB), and β-galactosidase and the Gene Amp RNA PCR kit (Perkin Elmer Cetus, Norwalk, Conn.) as previously described (Fink, D. J., 1992, *Human Gene Ther.* 3:11–19). Reverse transcription of the samples was carried out using AMV reverse transcripta3e and oligo dT at 42° C. for 15 min, 99° C. for 5 min, and 5° C. for 5 min. Reverse transcribed samples and RNA samples without reverse transcription (–RT) were used in standard PCR reactions using the gB or lacZ primer pairs according to the provided protocols. The specific reaction conditions used were: (i) initial denaturation 95° C. for 2 min; (ii) [anneal and extension 60° C. for 1 min, denaturation 95° C. for 1 min)×35 cycles; and (iii) final extension 72° C. for 10 min. PCR products were run on 5% acrylamide gels and gB- or lacZ-specific bands were detected as previously described (Fink, D. J., 1992, *Human Gene Ther.* 3:11–19). PCR reactions on viral DNA were performed in a similar manner without reverse transcription, as previously described (Fink, D. J., 1992, *Human Gene Ther.* 3:11–19).

6.2. RESULTS

Characterization of a promoter designated LAP2 immediately upstream of the 2.0 kb LAT. Two putative promoter constructs encompassing similar sequences lying upstream and extending into the left-hand portion of the 2.0 kb LAT were juxtaposed to the CAT reporter gene and examined for their ability to transiently express CAT following transfection of Vero cells. One construct was produced at the University of Michigan and spanned a region –800 to +42 bp relative to the 5' terminus of the 2 kb LAT (FIG. 1D) The second construct was cloned at the NIH and included sequences –819 to +839 relative to the stable LAT 5' end (FIG. 1E). Both laboratories also engineered large series of 5' deletions in order to search for regulatory elements which might influence promoter activity in transient CAT gene expression assays. The results of the CAT assays are also presented in FIGS. 1D and 1E.

In general, there was good agreement between the two independent CAT expression analyses employing similar sets of CAT reporter constructs. Constructs containing the region spanning –597 to –193 all displayed high levels (>20% acetylation) of activity. Both studies showed that progressive deletion between –193 and –14 led to a fairly progressive decrease in promoter activity although one region (–81 to –58) containing a C/T rich element more sharply reduced promoter activity upon removal, suggesting its importance to transcriptional control. Both studies revealed essentially basal promoter activity with constructs of –44 to –14. Promoter activity was lost completely by deletion up to +28 supporting the existence of a minimal promoter element located between –14 and +28. Some differences were observed near the transcription start site. For example, CAT activity was reduced in the –83 michigan construct whereas the –78 NIH construct retained activity, which may be due to the presence of an AP2 site or the abscence of the entire C/T element. Both analyses also showed that additional upstream sequences (–800/+42 or –819/+829) that encompass the TATA box, CRE (Leib, D. A., 1991, *Proc. Natl. Acad. Sci. USA* 88:48–52), and USF (Zwaagstra, J. C., 1991, *Virology* 182:287–297.) elements were less active than constructs lacking this region (–597/+42 or –597/+839). Since previous work (Batchelor, A. H., 1990, *J. Virol.* 64:3269–3279; Batchelor, A. H., 1992, *J. Virol.* 66:3573–3582; Devi-Rao, G. B., 1991, *J. Virol.* 65:2179–2190; Leib, D. A., 1991, *Proc. Natl. Acad. Sci. USA* 88:48–52; Zwaagstra, J. C., 1989, *T. Gen. Virol.* 70:2163–2169.; Zwaagstra, J. C., 1991, *Virology* 182:287–297; Zwaagstra, J. C., 1990, *J. Virol.* 64:5019–5028) had shown that the TATA box containing region is located within a promoter active in driving CAT expression in similar tranfection assays, the upstream promoter or some elements associated with it might be interfering with transcription of the downstream TATAless promoter.

Some internal deletions were also introduced into the Michigan construct to further define potential cis-acting promoter regulatory elements. Deletion of sequences between −196 to −289 resulted in an increase in CAT activity suggesting that either a repressor factor binds to this region or that by deleting this sequence other positive regulatory elements further upstream are brought into closer proximity to the minimal promoter sequences. However, deletion of sequence from −394 to −228 produced a construct with activity (17.8% Ac) comparable to that of the parental −597/+42 construct (19.7% Ac). Another internal deletion, lacking sequence from −394 to −196 caused approximately a two-fold reduction (9.4%Ac) in activity. Overall, experiments with these internal deletions, in combination with these involving the 5' deletions, indicate that the region between −200 and −400 plays a role in modulating the activity of the basal LAP2 promoter region located between −14 and +28. Analysis of the sequence within that area finds it to be extremely G+C rich, averaging 81% in comparison to about 72% throughout the remainder of the HSV $IR_L$ and $TR_L$ segments.

Identification of the 5' end of the LAP2 driven transcript produced in transient transfection assays. In order to map the 5' terminus of the chimeric LAT-CAT chimeric RNA produced during transient transfection assays, sensitive RNase protection analyses were performed using whole cell RNA isolated from Vero cells transfected with the −597/+42 LAP2-CAT construct and $^{32}$P-labeled riboprobes. Only the antisense (T7) probe produced a protected fragment of approximately 290 nucleotides when hybridized to RNA harvested from the −597/+42 LAP2-CAT transfected cells. These data place the 5' end of the chimeric LAT-CAT transcript at or near to the 5' end of the 2 kb LAT, since a band of 292 bp should have been seen if this chimeric RNA initiated at the +1 of the 2 kb LAT.

Comparison of the activity of LAP2 with LAP1 in transient transfection assays. In order to evaluate the level of expression detected with LAP2, chimeric promoter CAT constructs were used in transient transfection assays to compare LAP2 with LAP1. LAP1 was active in both normal and reverse orientations, whereas LAP2 was not active when reversed. The ability of LAP1 to function in the reverse orientation was seen in previous assays (Batchelor, A. H., 1990, J. Virol. 64:3269–3279) in agreement with our results. LAP2 (18.2% Ac) was four to fivefold less active than LAP1 (90.6–93.6% Ac) in this analysis. Dilution of the lysates to bring LAP1 activity within the linear range resulted in LAP2 being five to tenfold less active than LAP1 with LAPL2 being one-third less active than LAP1 in the normal orientation. These assays demonstrate that the LAP2 promoter region is active in transient assays, albeit at a lower level than LAP1.

Regulation of LAP2 by HSV transactivating gene products. Since other HSV promoters are transcriptionally activated by the ICP4 or ICPO immediate early gene products (Everett, R. D., 1984, EMBO J. 3:3135–3141; Gelman, I. H., 1985, Proc. Natl. Acad. Sci. USA 82:5265–5269; O'Hare, P., 1985, J. Virol. 53:751–760; Quinlan, M. P., 1985, Cell Biol. 5:957–963; Shapira, M., 1987, Nucl. Acids Res. 15:3097–3111), it was of interest to determine the response of LAP2 to these regulatory proteins. Cotransfection analyses were performed using equimolar amounts of the LAP2 reporter plasmid (−597/+42) and plasmids encoding either ICP4 (pSGEK1) (Quinlan, M. P., 1985, Cell Biol. 5:957–963) or ICPO (pIGA15) (Gelman, I. H., 1985, Proc. Natl. Acad. Sci. USA 82:5265–5269). The LAP2 reporter construct yielded high levels of CAT activity when transfected into Vero cells. When LAP2 was placed in the opposite orientation to the CAT reporter gene (+42/−597), CAT activity was not detected above the background levels produced by a promoterless CAT construct. Cotransfection with the ICP4 encoding plasmid resulted in a 50 fold reduction in the activity of the LAP2-CAT construct. In contrast, ICP4 activates all other HSV early and late promoters except for the large subunit of ribonucleotide reductase (RR1) (Wymer, J. R., 1989, J. Virol. 63:2773–2784). Cotransfection of an ICP0 expressing plasmid also produced a repressive effect on LAP2 activity, however the magnitude of the reduction in activity was less than that observed with ICP4. ICP0 has previously been shown to be a promiscuous transactivator capable of activating a variety of promoters examined in transient cell culture transfection experiments (Everett, R. D., 1987, Anticancer Res. 7:589–604; Goins, W. F., Unpublished data; Mosca, J. D., 1987, Proc. Natl. Acad. Sci. USA 84:7408–7412; Nabel, G. J., 1988, Science 239:1299–1302; Ostrove, J. M., 1987, J. Virol. 61:3726–3732). Cotransfection with both ICP4 and ICP0 encoding plasmids resulted in levels of CAT equivalent to those seen in cells transfected with the promoterless CAT construct. In transient assays with other HSV promoter reporter constructs, ICP4 and ICP0 have been shown to display synergistic transcriptional transactivating ability (Everett, R. D., 1984, EMBO J. 3:3135–3141; Everett, R. D., 1987, Anticancer Res. 7:589–604; Gelman, I. H., 1985, Proc. Natl. Acad. Sci. USA 82:5265–5269; O'Hare, P., 1985, J. Virol. 53:751–760; Quinlan, M. P., 1985, Cell Biol. 5:957–963; Shapira, M., 1987, Nucl. Acids Res. 15:3097–3111). In addition, transfection of the −597/+42 CAT followed by coinfection with wild-type HSV-1 strain KOS produced a reduction in CAT activity. This result could be due to the action of ICP4 and ICPO or due to the action of other proteins encoded by the virus during acute infection.

Regulation of LAP2 by ICP4. Since the activity of LAP2 was reduced by coexpression of ICP4, further assays were designed to evaluate the unique response of LAP2 to ICP4. Cotransfection assays using LAP2 5' deletion constructs and equimolar amounts wild-type ICP4 were performed to identify any possible cis-elements in LAP2 that were negatively responsive to ICP4. All three constructs containing varying amounts of LAP2 sequence (−597/+42, −171/+42 and −38/+42) were active alone yet down-regulated markedly in the presence of ICP4, as previously seen. Since the minimal promoter reporter construct (−38/+42) which contains sequences necessary for LAP2 basal activity (−14/+28) was repressed by ICP4, this minimal promoter sequence probably includes the target for the action(s) of ICP4. It is possible that either ICP4 is binding to this region and preventing initiation of transcription from LAP2 or that ICP4 is interacting with transcription factors and thereby making them less accessible to LAP2.

In order to further evaluate the role of ICP4 in repressing LAP2 activity, cotransfection assays were conducted with wild-type ICP4 and Tn5 insertion mutants of ICP4. Tn5 is a prokaryotic transposable element possessing a kanamycin resistance marker flanked by inverted terminal repeat sequence (deBruijn, F. J., 1984, Gene 27:131–149). Tn5 insertion into DNA sequences encoding a specific polypeptide results in truncation of the corresponding gene product due to the presence of amber translation termination codons located within the transposon termini in all three reading frames. This method has been previously employed to disrupt the twelve Us genes of HSV to examine the role of these ORFs in the neuropathogenesis of HSV infection in vivo (Weber, P. C., 1987, Science 236:576–579). A panel of Tn5 insertion/truncation mutants of ICP4 were produced, the insertion sites approximated by analysis of restriction enzyme digest patterns and their ability to repress the activity of LAP2 was assessed in transient cotransfection assays. For comparison, the ability of the ICP4/Tn5 mutants to transactivate the HSV glycoprotein C (gC) late gene promoter was also evaluated. Both LAP2 and the gC promoter were active in driving the CAT reporter gene. However their response to wild-type ICP4 and the Tn5 mutants differed. Although wild-type ICP4 was able to further activate the gC promoter, it produced a reduction in activity of the LAP2 construct. This result with LAP2 was similar to that obtained in previous assays. The ICP4 Tn5 mutant #15 failed to repress the activity of LAP2 compared to wild-type ICP4. In addition, Tn #15 was unable to transactivate the HSV gC promoter. Previously we have seen that ICP4 Tn5 mutant #15 was unable to transactivate other HSV lytic gene promoters (Weber, P. C., Unpublished data). Another ICP4 Tn5 mutant, Tn5 #23, produced results similar to those found using wild-type ICP4, i.e., repressing LAP2 and activation of the gC promoter. Previously this mutant was observed to transactivate other HSV lytic gene promoters such as thymidine kinase (tk) and glycoprotein D (gD) (Weber, P. C., Unpublished data). These results rule out promoter competition as a method for the down-regulation of LAP2 since ICP4 Tn5 mutant #15 was unable to repress LAP2 in these assays. In addition, cotransfection of plasmids expressing ICP22, ICP47 or VP16 failed to repress LAP2. Together, these results show that the ability of ICP4 to downregulate LAP2 involves the very same domains of the protein that are involved in transactivation of other HSV lytic gene promoters.

In vivo activity of LAP2. In order to examine the activity of LAP2 in vivo, it was necessary to juxtapose LAP2 to the lacZ reporter gene and introduce this promoter-reporter gene cassette into the HSV genome. The −597/+42 LAP2 (PstI to BamHI) construct was selected to drive activity of the lacZ reporter gene because of its high level of activity in transient expression assays. The LAP2-lacZ cassette was then subcloned into a plasmid containing gC flanking sequence in order to introduce it into the viral genome by homologous recombination in marker transfer experiments. By cloning LAP2lacZ into this gC plasmid, the gC promoter sequences were removed insuring that expression of the lacZ reporter gene was controlled by LAP2. This construct was recombined into the genomes of both wild-type KOS and the ICP4mutant d120 to produce the constructs gC−::LAP2-lacZ and d120 (ICP4−), gC-::LAP2-lacZ respectively. Diagrams of the viral constructs and the Southern blots of these recombinants are shown in FIG. 7.

The d120 (ICP4−),gC-::LAP2-lacZ recombinant was used to infect cells in culture to examine the activity of LAP2. Vero cells were examined as well as a rat neuroma cell line (B103). The cells were infected at low MOIs and stained with X-gal to detect the expression of the lacZ reporter gene. Individual Vero cells stained positive for lacZ at both 2 and 5 days postinfection (FIG. 8A). When the ICP4 inducible E5 cell line (DeLuca, N. A., 1985, *J. Virol.* 56:558–570) was used, no lacZ positive cells were detected, consistant with the results of the transient cotransfection assays. To determine whether LAP2 was active in neurons, the B103 rat neuroma cell line was also infected with the viral recombinant and positive staining blue neurons were observed. The negative control parental virus, d120 (ICP4−), never produced lacZ positive staining blue cells regardless of which cell type was examined.

The in vivo LAP2 activity from the viral genome in neurons of the peripheral nervous system (PNS) was evaluated following corneal scarification of A/J strain mice using the gC−::LAP2-lacZ recombinant. This recombinant replicates in standard cell culture yet does not produce blue plaques following X-gal agarose overlay. This recombinant was able to replicate in corneal epithelial cells following corneal scarification yet failed to produce lacZ from LAP2 in these cells. The trigeminal ganglia (TG) of infected animals were removed, sectioned and stained with X-gal at various times post-inoculation. No lacZ positive staining neurons were detected between 2 and 5 days post inoculation, a time at which viral lytic gene antigens were detected. Previously, another virus recombinant containing the lacZ reporter gene driven by the lytic gC late gene promoter in the US3 gene locus, US3-::pgC-lacZ, was reported to stain positive for β-gal in TG neurons at 2 to 5 days yet was negative by 7 days postinfection (Hill, T. J., 1985, The herpesviruses, Vol. 3). Infection with the gC−::LAP2-lacZ recombinant did, however, produce lacZ positive staining TG neurons at 7 days post-inoculation, a time at which lytic gene expression ceases. β-gal positive neurons displayed a punctate staining pattern within the cytoplasm similar both to that observed in cell culture and to that reported by Ho and Mocarski (Ho, D. Y., 1989, *Proc. Natl. Acad. Sci. USA* 86:7596–7600) using a similar virus recombinant. β-gal positive neurons were also detected at 150 to 300 days post-infection, a time consistent with HSV latent infection. X-gal staining for β-gal expression was confirmed by immunohistochemical staining with anti-β-galactosidase antibody. To confirm that the X-gal staining was the result of LAP2 driven expression of the lacZ reporter gene, sensitive RT-PCR assays were performed on RNA isolated from d120 (ICP4−),gC-::LAP 2-lacZ infected rat TGs at 7 and 21 d.p.i. using a lacZ specific primer pair which we have previously used in similar in vivo RT-PCR assays (Fink, D. J., 1992, *Human Gene Ther.* 3:11–19). A 324 bp lacZ specific band was detected using RNA isolated from independent animals at both 1 and 3 weeks, whereas RT-PCR for glycoprotein B (gB) failed to detect a gB specific message at these times post infection. In addition, DNA PCR was positive for the presence of the viral genome at 21 days post-infection, while RNA samples that were not reverse transcribed (−RT) produced no signal, suggesting that the RNA PCR products were the result of DNA contamination further confirming the specificity of the signal detected. Together, these data show that LAP2 is active in the context of the viral genome at times consistent with HSV latency.

6.3. Sequence Listing

The sequence of the LAP2 region is given hereinafter as SEQ ID No:1. Base 1 of the SEQ ID No:1 corresponds to −600 of the LAP2 numbering system (600 bp 5' of the 5' terminus of the LAT).

We claim:

1. A herpes simplex virus type 1 comprising
    (a) a LAP2 promoter encoded by SEQ ID NO:1, or fragments of SEQ ID NO:1 which have LAP2 promoter activity; and
    (b) a heterologous DNA sequence of interest operably linked to said promoter inserted within the genome of said HSV-1.

2. The virus of claim 1 which further comprises a mutation in or deletion of a gene of the virus that is essential for replication of the virus.

3. The virus of claim 1, wherein the promoter of claim 1 and the heterologous gene are inserted into a herpes virus gene that is expressed during productive infection.

4. The virus of claim 3 wherein the LAP2 promoter contains a deletion in the region between 289 and 196 bp 5' of the LAT transcription initiation site.

5. The virus of claim 3 wherein the non-herpes protein is neurotrophic factor.

6. The virus of claim 5 wherein the neurotrophic factor is selected from the group consisting of nerve growth factor, ciliary neurotrophic factor, brain derived neurotrophic factor, glial derived neurotrophic factor and neurotrophin-3.

7. The virus of claim 3 wherein the non-herpes protein is neurotrophic factor receptor.

8. The virus of claim 7 wherein the receptor is selected from the group consisting of nerve growth factor receptor, ciliary neurotrophic factor receptor, brain derived neurotrophic factor receptor, glial derived neurotrophic factor receptor and neurotrophin-3 receptor.

9. The virus of claim 3 wherein the non-herpes protein is preproenkephalin.

10. The virus of claim 3 wherein the non-herpes protein is a superoxide dismutase.

11. The virus of claim 3 wherein the non-herpes protein is an androgen receptor.

12. The virus of claim 1, wherein said LAP2 promoter comprises a deletion mutant of SEQ ID NO:1.

\* \* \* \* \*

UNITED STATES PATENT AND TRADEMARK OFFICE
CERTIFICATE OF CORRECTION

PATENT NO. : 5,849,571

DATED : December 15, 1998

INVENTOR(S) : Glorioso, Joseph C.; Fink, David J.; Goins, William F.

It is certified that errors appear in the above-identified patent and that said Letters Patent is hereby corrected as shown below:

IN THE SPECIFICATION:

In Column 2, line 12, "stand" should read --strand--.

In Column 4, line 35, "of" should be deleted.

In Column 4, line 43, "dspicts" should read --depicts--.

In Column 4, line 44, "nutants" should read --mutants--.

In Column 4, line 50, "parts" should be deleted.

Figure 2:
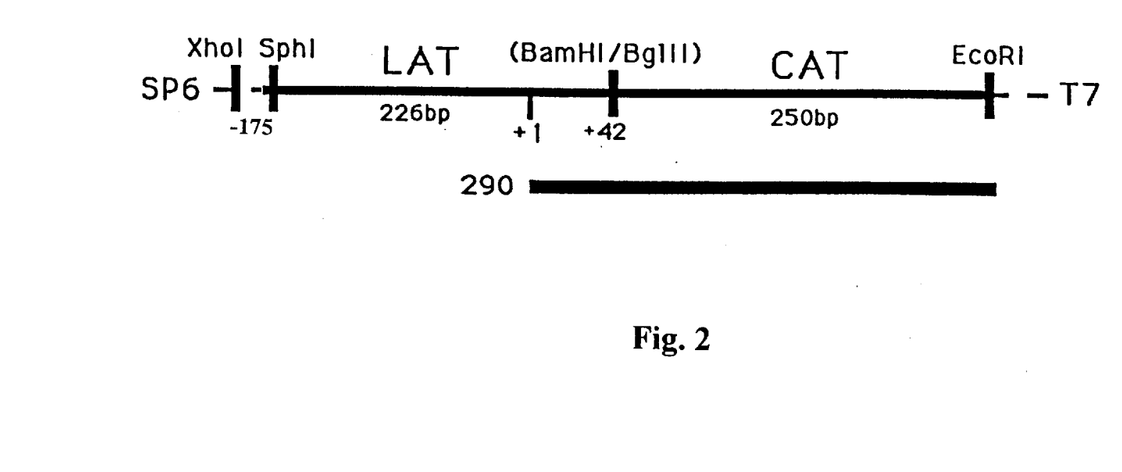
FIG. 2 is a schematic representation depicting the FIG. 2. RNase protection assay on RNA isolated from Vero cells transfected with the −597/+42 LAP2-CAT construct. A region of the −597/+42 LAP2-CAT construct, from the SphI site at −171 of LAT to the EcoRI site at +250 into the CAT sequence, which was subcloned into the SphI/EcoRI sites within the polylinker of pSP72 to produce riboprobes for RNase protection experiments.
Figure 3:
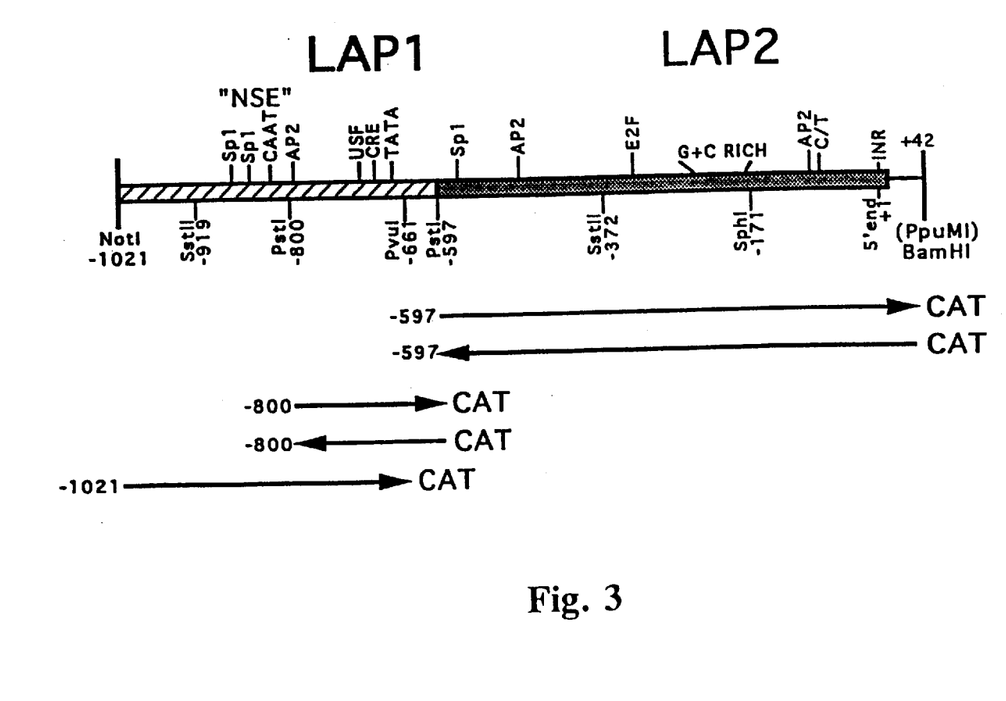
FIG. 3 is a schematic comparison of the TATA-less LAP2 promoter with the LAP1 TATA-box containing promoter used in transient transfection analysis. Representative constructs containing LAP2 promoter sequence (−597/+42) linked to CAT were compared to CAT constructs with varying amounts of LAP1 (−1021/−661 and −800/597) sequence in transient transfection assays in Vero cells. In addition, constructs containing LAP1 (−597/−800) and LAP2 (+42/−597) sequence in the reverse orientation were used as controls, as was a promoterless CAT construct.

In Column 4, lines 52-54, "FIG. 2. RNase protection assay on RNA isolated from Vero cells transfected with the -597/+42 LAP2-CAT construct. A" should be deleted.

In Column 6, line 12, "be" should be deleted.

In Column 6, line 26, "muatation" should read --mutation--.

In Column 6, line 33, "tisseus" should read --tissues--.

In Column 7, line 64, "FIG. 1, Part D" should read --FIG. 1D--.

In Column 9, line 17, "µgs" should read --µg--.

In Column 9, line 32, "µgs" should read --µg--. In Column 10, line 5, "polya" should read --poly A--.

UNITED STATES PATENT AND TRADEMARK OFFICE
CERTIFICATE OF CORRECTION

PATENT NO. : 5,849,571
DATED : December 15, 1998
INVENTOR(S) : Glorioso, Joseph C.; Fink, David J.; Goins, William F.

It is certified that errors appear in the above-identified patent and that said Letters Patent is hereby corrected as shown below:

IN THE SPECIFICATION:

In Column 10, line 13, "2 µg" should read --21 µg--.

In Column 10, line 24, "50 µg" should read --50 µl--.

In Column 11, line 20, "Ind." should read --IA--.

In Column 11, line 23, "1x1o5PFU" should read --1x10$^5$ PFU--.

In Column 11, line 45, "weight)," should read --weight).--.

In Column 11, line 63, "transcripta3e" should read --transcriptase--.

In Column 12, line 44, "michigan" should read --Michigan--.

In Column 12, line 47, "abscense" should read --absence--.

In Column 13, line 46, "LAPL2" should read --LAP2--.

In Column 15, line 45, "ICP4mutant" should read --ICP4 mutant--.

Signed and Sealed this

Twenty-eighth Day of December, 1999

*Attest:*

Q. TODD DICKINSON

*Attesting Officer*   *Acting Commissioner of Patents and Trademarks*